United States Patent [19]
LeBlanc et al.

[11] Patent Number: 6,083,387
[45] Date of Patent: Jul. 4, 2000

[54] APPARATUS FOR THE DISINFECTION OF FLUIDS

[75] Inventors: Edward L. LeBlanc; Jeffrey C. Burnham, both of Naples, Fla.; Walter F. Emig, III, Fenton, Mich.

[73] Assignee: Burnham Technologies Ltd., Naples, Fla.

[21] Appl. No.: 08/667,028

[22] Filed: Jun. 20, 1996

[51] Int. Cl.$^7$ .............................. B01J 19/08; B01J 19/12; B01D 15/00
[52] U.S. Cl. .................. 210/199; 422/186.3; 250/432 R
[58] Field of Search ........................ 422/186.03; 210/748, 210/199; 250/432 R, 435

[56] References Cited

U.S. PATENT DOCUMENTS

| | | |
|---|---|---|
| 2,147,857 | 2/1939 | O'Brein . |
| 2,340,890 | 2/1944 | Lang et al. . |
| 3,230,137 | 1/1966 | Ellison . |
| 3,433,946 | 3/1969 | Hardwick . |
| 3,456,107 | 7/1969 | Robertson . |
| 3,462,597 | 8/1969 | Young . |
| 3,471,693 | 10/1969 | Veloz . |
| 3,485,576 | 12/1969 | McRae et al. . |
| 3,527,940 | 9/1970 | Balanca et al. . |
| 3,550,782 | 12/1970 | Veloz . |
| 3,562,520 | 2/1971 | Hippen .................................... 250/372 |
| 3,634,025 | 1/1972 | Landry .................................... 250/436 |
| 3,659,096 | 4/1972 | Kompanek ............................... 422/24 |
| 3,674,421 | 7/1972 | Decupper . |
| 3,683,177 | 8/1972 | Veloz ....................................... 250/435 |
| 3,700,406 | 10/1972 | Landry . |
| 3,767,918 | 10/1973 | Graybeal ................................. 250/436 |
| 3,814,680 | 6/1974 | Wood . |
| 3,837,800 | 9/1974 | Wood ....................................... 422/24 |
| 3,889,123 | 6/1975 | Bosshard .................................. 378/67 |
| 3,894,236 | 7/1975 | Hazelrigg ................................ 250/435 |
| 3,923,663 | 12/1975 | Reid ........................................ 210/251 |
| 3,948,772 | 4/1976 | Ellner ..................................... 210/96.1 |
| 4,008,045 | 2/1977 | Free ........................................ 250/436 |
| 4,017,735 | 4/1977 | Siegel ..................................... 250/430 |
| 4,028,246 | 6/1977 | Lund ....................................... 210/151 |
| 4,141,686 | 2/1979 | Lewis ...................................... 250/436 |
| 4,141,830 | 2/1979 | Last ........................................ 210/748 |
| 4,189,363 | 2/1980 | Beitzel ................................... 204/158.2 |
| 4,214,962 | 7/1980 | Pincon .................................. 204/157.44 |
| 4,230,571 | 10/1980 | Dadd ....................................... 210/760 |
| 4,273,660 | 6/1981 | Beitzel .................................... 210/760 |
| 4,274,970 | 6/1981 | Beitzel .................................... 210/748 |
| 4,296,066 | 10/1981 | Schenck .................................... 422/24 |
| 4,336,223 | 6/1982 | Hillman .................................... 422/24 |
| 4,367,410 | 1/1983 | Wood ...................................... 250/431 |
| 4,372,860 | 2/1983 | Kaas ....................................... 210/748 |
| 4,396,582 | 8/1983 | Kodera ................................... 422/300 |
| 4,400,270 | 8/1983 | Hillman ................................... 210/103 |
| 4,438,337 | 3/1984 | Forrat .................................... 250/436 |
| 4,467,206 | 8/1984 | Taylor .................................... 250/435 |
| 4,469,835 | 9/1984 | Laurin ..................................... 524/349 |
| 4,471,225 | 9/1984 | Hillman ................................... 250/436 |
| 4,482,809 | 11/1984 | Maarschalkerweerd ............... 250/436 |
| 4,534,282 | 8/1985 | Marinoza ................................. 99/451 |
| 4,602,162 | 7/1986 | Sperry, III et al. .................... 250/436 |
| 4,615,799 | 10/1986 | Mortensen .............................. 210/177 |
| 4,694,179 | 9/1987 | Lew et al. .............................. 250/431 |
| 4,751,392 | 6/1988 | Wiesmann ............................... 250/429 |
| 4,752,401 | 6/1988 | Bodenstein ............................... 210/746 |
| 4,757,205 | 7/1988 | Latel ....................................... 250/435 |
| 4,766,321 | 8/1988 | Lew et al. .............................. 250/431 |
| 4,767,932 | 8/1988 | Ellner ..................................... 250/435 |
| 4,769,131 | 9/1988 | Noll et al. .............................. 210/85 |
| 4,798,702 | 1/1989 | Tucker ..................................... 422/24 |
| 4,849,115 | 7/1989 | Cole et al. ............................. 210/748 |
| 4,857,204 | 8/1989 | Joklik ..................................... 210/695 |
| 4,866,282 | 9/1989 | Miripol et al. ....................... 250/455.11 |
| 4,872,980 | 10/1989 | Maarschalkerweerd ............... 210/243 |
| 4,897,246 | 1/1990 | Peterson ................................ 422/186.3 |

(List continued on next page.)

FOREIGN PATENT DOCUMENTS

| | | |
|---|---|---|
| 0317735 | 5/1989 | European Pat. Off. . |
| 2450612 | 4/1980 | France . |
| 4233566A1 | 3/1994 | Germany . |
| WO9509815 | 10/1994 | WIPO . |

OTHER PUBLICATIONS

Database WPI, Section Ch, Week 9333, Derwent Abstract No. XP002061140, Derwent Publications, Ltd., London, GB.

Database WPI, Section Ch, Week 9119, Derwent Abstract No. XP002061141, Derwent Publications, Ltd., London, GB.

Database WPI, Section Ch, Week 8716, Derwent Abstract No. XP002061142, Derwent Publications, Ltd., London, GB.

*Primary Examiner*—Lila Feisee
*Assistant Examiner*—Michael Pak
*Attorney, Agent, or Firm*—Baker & Botts LLP

[57] ABSTRACT

This invention relates to apparatus and methods for the disinfection of fluids and, in particular, to the disinfection of industrial fluids with ultraviolet radiation. These fluids are typically used in manufacturing as coolants in both long and short assembly lines. They commonly accumulate contaminants from multiple and diverse sources including oil and microorganisms. Fluids can be disinfected by establishing a fluid flow rate sufficient to prevent occlusion of the walls of the ultraviolet transmissible portion by contaminants. Fluids may be so heavily contaminated as to require removal of at least a minimum percentage of contaminants (MPC) prior to irradiation. Such fluids may be processed to remove the minimum percentage of contaminants according to the equation: $MPC=102-(23.45 \times \ln V)$. Subject to removal of the MPC, a flow rate can be established to prevent occlusion of ultraviolet-transmissible portions of the flow path and thereby successfully treat the fluid with a disinfecting amount of ultraviolet radiation. Using these methods, microorganism levels can be greatly reduced with a reduced need for biocides or other anti-bacterial or anti-fungal agents. The methods and apparatus of the invention also comprise a flattened-tube mechanism for increased exposure to UV radiation and a turbulence-generating system to increase effectiveness of radiation treatments. Turbulence-generating systems include means for creating pressure differentials or aeration in the fluid stream as well as various types of structures such as ribbons, paddles, cones, beads or vanes that can be placed within the lumen of the tubing system. These methods are highly effective at extending the useful life of fluids such as coolants and reducing or eliminating the risks posed to workers by heavily contaminated or biocide-treated coolants.

21 Claims, 9 Drawing Sheets

U.S. PATENT DOCUMENTS

| | | | |
|---|---|---|---|
| 4,904,874 | 2/1990 | Ellner | 250/436 |
| 4,909,931 | 3/1990 | Bibi | 210/85 |
| 4,952,376 | 8/1990 | Peterson | 250/186.3 |
| 4,952,812 | 8/1990 | Miripol et al. | 250/455.11 |
| 4,968,437 | 11/1990 | Noll et al. | 210/748 |
| 4,968,891 | 11/1990 | Jhawar et al. | 250/438 |
| 4,971,687 | 11/1990 | Anderson | 210/85 |
| 4,983,307 | 1/1991 | Nesathurai | 210/748 |
| 5,006,244 | 4/1991 | Maarschalkerweerd | 210/243 |
| 5,019,256 | 5/1991 | Ifill et al. | 210/232 |
| 5,026,477 | 6/1991 | Yen | 210/169 |
| 5,120,450 | 6/1992 | Stanley, Jr. | 210/748 |
| 5,178,758 | 1/1993 | Hwang | 210/256 |
| 5,230,792 | 7/1993 | Sauska et al. | 210/97 |
| 5,234,606 | 8/1993 | Kazama et al. | 210/748 |
| 5,258,124 | 11/1993 | Bolten et al. | 210/748 |
| 5,266,215 | 11/1993 | Engelhard | 210/748 |
| 5,288,461 | 2/1994 | Gray | 422/24 |
| 5,322,569 | 6/1994 | Titus et al. | 134/1 |
| 5,332,388 | 7/1994 | Schuerch et al. | 422/291 |
| 5,352,359 | 10/1994 | Nagai et al. | 210/192 |
| 5,366,705 | 11/1994 | Reidy | 422/243 |
| 5,368,826 | 11/1994 | Weltz et al. | 422/243 |
| 5,376,281 | 12/1994 | Safta | 210/748 |
| 5,433,738 | 7/1995 | Stinson | 607/92 |
| 5,439,595 | 8/1995 | Downey, Jr. | 210/748 |
| 5,494,585 | 2/1996 | Cox | 210/748 |
| 5,503,800 | 4/1996 | Free | 422/24 |
| 5,504,335 | 4/1996 | Maarschalkerweerd | 250/435 |
| 5,505,904 | 4/1996 | Haidinger et al. | 422/24 |
| 5,626,768 | 5/1997 | Ressler et al. | 210/748 |

Flow Direction ⟶

APPARATUS FOR THE DISINFECTION OF FLUIDS

BACKGROUND OF THE INVENTION

1. Field of the Invention

This invention relates to apparatus and methods for the disinfection of fluids and, in particular, to the disinfection of opaque industrial fluids with ultraviolet radiation.

2. Description of the Background

Coolant use in America's heavy industries has been a story of significant successes and failures. The efficacy of coolants in prolonging the life of various tools used in manufacturing has been high. This is due, in part, to the inclusion of specific organic and surfactant compounds that lubricate the materials and minimize oxidation damage and surface buildup of constituent substances on the tools. These compounds, as well as contaminating tramp oils that leak into the coolant from multiple sources, provide a very suitable nutrient base for microbial growth.

Coolants, as well as other industrial fluids, have traditionally possessed a fairly short useful life and need to be replenished often or even completely replaced. Although potentially toxic biocidal chemicals can be added to inhibit microbial growth, the biocidal effect eventually fails and supplementation with further biocides becomes impractical. Consequently, useful coolant life is only slightly extended. In addition, there are considerable environmental problems associated with disposal of used coolant, due in large part to the presence of these additives and other contaminants.

Over the past 50 years, machine coolant has been disposed of by dumping in drains, sewers and rivers, causing extensive and prolonged environmental ground pollution. In 1976, the EPA ruled that all oil-based coolants were contaminated waste and must be treated or a new way of disposal found (Public Law 94-580; Oct. 21, 1976). To accomplish this, centrifugation or filtration were considered as primary alternatives. Although filtration could remove some contaminant, filters often clogged or broke requiring more overall costs than would have been incurred by simply replacing the coolant. In addition, a successful filtration process only prolonged the life of the coolant by about two or three weeks making overall savings minimal. Centrifugation has been the principal mechanism for removing contaminated oils in larger machine tool plants. While centrifugation as an oil removal technique has a limited treatment rate, it has been used to reduce concentrations of contaminants, usually to about two percent. However, this partial removal does not prevent bacterial regrowth or breakdown of coolant and oil components.

Ultraviolet (UV) treatment has been used to disinfect clear waters and some wastewater as shown in U.S. Pat. Nos. 3,634,025; 3,700,406; 3,837,800; 3,889,123, 3,894,236; 4,471,225 and 4,602,162. Each of these U.S patents describes a method touted to be designed to sterilize water-based fluids. The principal idea behind this technique was that UV radiation would penetrate the clear liquid to kill offending microorganisms. The conventional technology of UV treatment is limited because total quartz systems have a tendency to foul easily and maintenance costs were high. UV treatment proved to be unsuccessful for industrial fluids such as coolants, as coolants are opaque, or substantially so, and often contain significant levels of contaminants such as hydraulic and way oils which are highly occlusive to ultraviolet light. Under these constraints, ultraviolet radiation cannot pass more than a very small distance, if at all, into the fluid stream (e.g. U.S. Pat. No. 3,456,107). These contaminants and coolants blocked UV transmission directly and also indirectly by adhering to wall surfaces of submerged quartz UV lamps or to the inner surfaces of the UV transmissible tubing in a dry system design, wherein UV lamps are kept separated from the fluid being treated.

A number of measures to prevent the degradation of coolant by microorganisms have been attempted with the objective to prolong the life of the coolant and to reduce odors and health risks associated with coolant spoilage. To minimize these risks and the hazards of contaminated coolant fluids, many facilities add appreciable levels of various biocides to coolant fluids to kill and inhibit the growth of microorganisms (e.g. U.S. Pat. No. 3,230,137). In general, coolants perform properly in the presence of these additives. However, allergic reactions to the biocides were common. In many cases, the biocides interacted with the skin of workers and caused various forms of hypersensitivity and dermatitis. In short, although bacterial counts can be reduced over the short term, biocides were often more problematic than the microorganisms themselves. Ultimately, the microorganisms overcome the biocides and the microbial degradation of coolant and contaminants results in foul odors in the work environment.

Conventional techniques, although useful in the short term, do not provide long term reduction of microbial counts in large industrial systems by more than a single log and, more importantly, only prolong coolant life for a short period despite their high cost. Other techniques such as aeration of coolant and thorough cleaning of the lines and machines through which the coolant flows proved to be largely unsuccessful in maintaining low levels of bacterial populations. Bacteria regrow in this environment due to the presence of available nutrients, and overcome inhibitory factors introduced by aeration or chemical management. Ultimately, the bacteria take hold throughout the coolant system.

Other, newer methods for the disinfection of coolant include pasteurization. In this process, coolant is heated to a pasteurizing temperature for a required period of time and subsequently cooled to an operating temperature. This process is energy intensive and the costs, resulting from the heating and cooling steps, are high. Although attempts have been made to keep pasteurization temperatures below the critical temperature that would destroy or denature the coolant, constant temperature cycling negatively effects coolant components. Consequently, there is a strong need for a safe and environmentally friendly method for the disinfection of industrial and other fluids.

SUMMARY OF THE INVENTION

The present invention overcomes the problems and disadvantages associated with current strategies and designs and provides new apparatus and methods for the disinfection of fluids.

One embodiment of the invention is directed to methods for disinfecting a fluid. The method comprises exposing the fluid to ultraviolet radiation after removing at least a minimum percentage of contaminants (MPC) necessary to permit effective disinfection according to the equation: $MPC = 102 - (23.45 \times \ln V)$; wherein V is the flow rate of the fluid being exposed to ultraviolet radiation. The method is useful for the treatment of opaque and substantially opaque fluids such as industrial fluids including coolants, machine fluids, bath fluids, process fluids and washing solutions.

Another embodiment of the invention is directed to methods for disinfecting a contaminated fluid in a flow path.

Fluid is pumped through the portion of the flow path exposed to a disinfecting amount of ultraviolet radiation at a rate sufficient to prevent adhesion of contaminants to UV transmissible surfaces within that portion.

Another embodiment of the invention is directed to methods for disinfecting a contaminated fluid in a flow path. These methods comprise passing the fluid through a portion of the flow path and generating turbulence within that portion. Turbulent fluid is exposed to a disinfecting amount of ultraviolet radiation. Turbulence can be generated by pumping pressurized fluids such as a gas or a liquid through the flow path. Alternatively, turbulence can be generated by placing obstacles within the flow path. Such obstacles include ribbon, beads, cones, vanes and combinations of these structures.

Another embodiment of the invention is directed to apparatus for disinfecting an industrial fluid. The apparatus is comprised of a tubing system for guiding the passage of the industrial fluid at a flow rate (V) through the apparatus. The tubing system comprises an ultraviolet-transmissible portion having a flattened to rounded cross section. The apparatus further comprises a contaminant separation system for removing at least a minimum percentage of contaminants from the fluid according to the equation: MPC=102−(23.45× lnV). The contaminated fluid is then exposed to an ultraviolet radiation system. The ultraviolet radiation system comprises a plurality of ultraviolet lamps and, optionally, reflectors to direct UV radiation in close proximity to the fluid flow as a dry modular apparatus.

Another embodiment of the invention is directed to apparatus for disinfecting an industrial fluid. The apparatus comprises a tubing system for guiding the industrial fluid through the apparatus at a flow rate (V) through the apparatus. The tubing system is comprised of ultraviolet-transmissible tubing having a flattened to rounded cross section. The apparatus further comprises a turbulence-generating system for creating turbulence with a Reynolds number or turbulence characteristic above that defining laminar flow, within the fluid during irradiation. Turbulence generating means include techniques such as placing intratubular paddles, beads, cones or vanes within the tubing, or creating a pressure differential or aeration within the tubing. Turbulence moves target microorganisms from UV-free zones within the interior of the tube to the surface of the fluid at the tube where they are killed upon exposure to UV radiation. Turbulence also serves as a scouring force to prevent contaminants from adhering to tube and/or lamp surfaces. Turbulent fluid is than irradiated from ultraviolet radiation system comprised of a plurality of ultraviolet lamps in close proximity to the fluid. The apparatus may further contain a contaminant separation system for removing at least a minimum percentage of contaminants from the fluid according to the equation: MPC=102−(23.45×lnV).

Another embodiment of the invention is directed to fluids disinfected by the methods and apparatus of the invention. Such fluids include beverages and industrial liquids such as coolants and other lubricants.

Other embodiments and advantages of the invention are set forth in part in the description which follows, and in part, will be obvious from this description, or may be learned from the practice of the invention.

DESCRIPTION OF THE INVENTION

Figure 1:
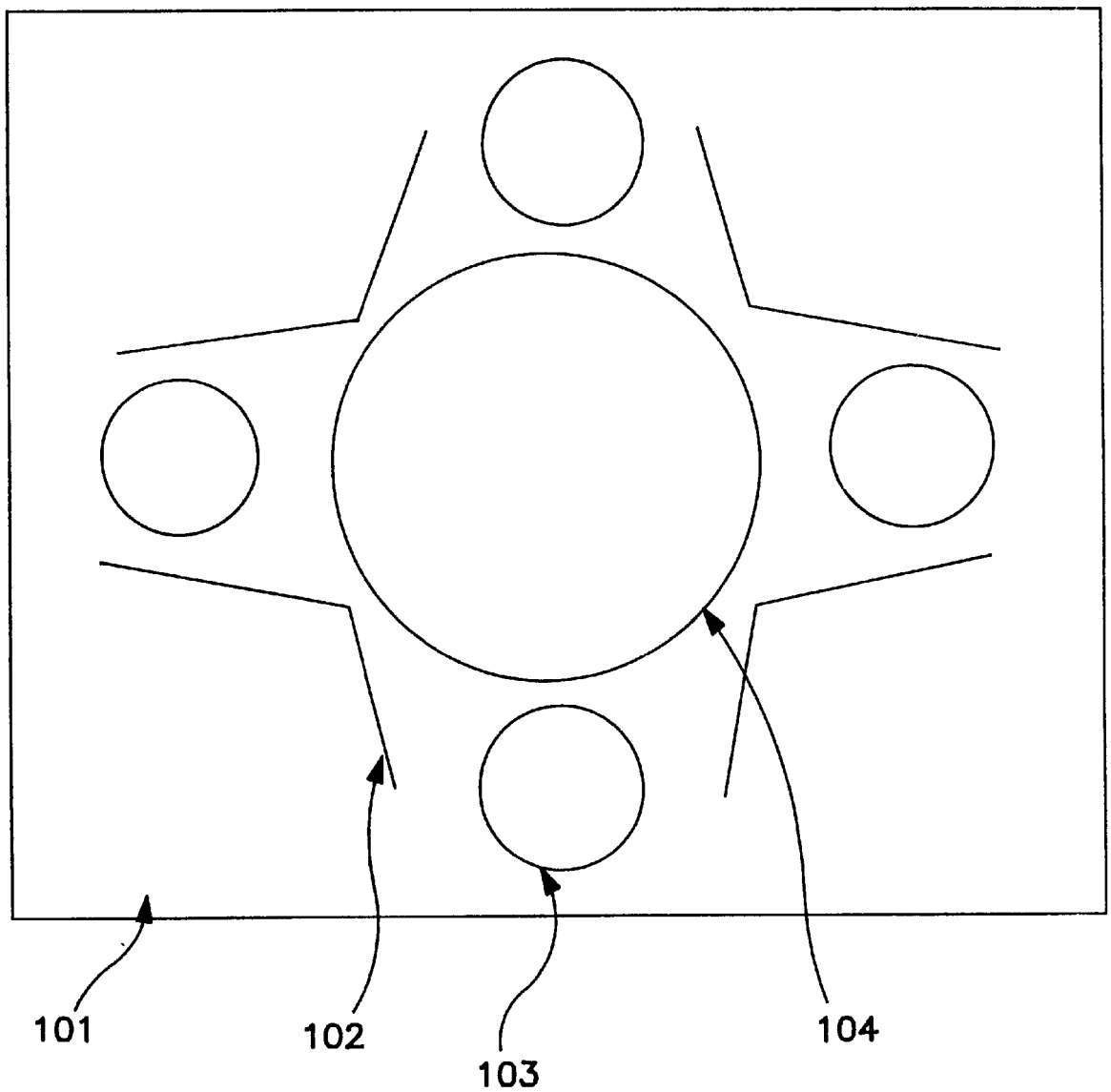
FIG. 1 Concept of a dry modular UV disinfection system.

As embodied and broadly described herein, the present invention is directed to apparatus and methods for the disinfection of fluids with ultraviolet radiation.

In an industrial setting, metal particles and way oils heavily contaminate coolants in assembly and manufacturing lines. In a packing plant, fruit juices and soft drinks become contaminated with microorganisms such as bacteria and yeast or other types of fungi. Other contaminants enter the fluid as it proceeds through various mixing and bottling systems. These and other contaminants serve as an abundant nutrient base in which microorganisms flourish.

Conventional methods for the disinfection of fluids include membrane filtration to remove microorganisms or pasteurization or the addition of chemicals, antibiotics or other additives to kill and/or inhibit proliferating microorganisms in the fluid. These methods, although useful in the short term, provide few long term benefits and pose serious problems of their own. Filtration, usually effective for controllable flows of water, is usually impractical for the disinfection of industrial fluids. These fluids contain significant amounts of oil and debris as contaminants. Such fluids include metal-working fluids and other machine-tool lubricants and coolants. These fluids contain components essential to their function that would be filtered out along with any unwanted contaminants or would require multiple filtration steps and filter changes, making the filtration process impractical. Adding chemicals presents health risks to workers, as well as to the environment, and can reduce coolant efficiency. Repeated pasteurization can denature the molecular structure of components of the fluid, thereby reducing coolant efficacy. Methods such as exposure to UV radiation, useful for UV transparent fluids, have proven to be ineffective for non-UV transparent (opaque) fluids with oil and other contaminants.

It has been discovered that microbially contaminated fluid can be disinfected by ultraviolet radiation when the flow of fluid through the disinfection step is above a set rate. In this manner, microbial contamination of fluids, such as UV-opaque and industrial fluids, can be substantially reduced or eliminated by treating the fluid with ultraviolet radiation. Substantially reduced means that microbial contamination is reduced such that useful life of the coolant is extended or the concentration of biocide needed to prevent microbial growth is lowered. Above a set critical level of contaminants, a minimum percentage of contaminants (MPC) can be removed from the fluid before the disinfecting properties of UV radiation can be successfully administered. MPC is a variable which is dependant on the velocity of the fluid as it proceeds through the radiation treatment. The more rapid the rate of fluid flow, the less the amount of contaminants that need to be removed. The lower the flow rate, the greater the amount of contaminants that must be removed. As flow rate can be controlled, the MPC can be determined for most any fluid.

One embodiment of the invention is directed to a method for the disinfection of a fluid with an ultraviolet radiation treatment system. A successful process is dependent on maintaining at least a minimum flow of fluid in the system. This flow rate is required, in part, to prevent occlusion that interferes with the transmission of UV energy to the microorganisms. Interference can be in the form of occlusion on the inner walls of the tubing of a dry disinfection system or the outer walls of quartz-jacketed ultraviolet lamps in a submerged disinfection system.

In some cases it may not be possible or desirable to achieve fluid flow rates high enough to prevent occlusion. In these cases, occlusion can be controlled by removing at least a minimum percentage of contaminants from the fluid. That MPC can be represented by the function of the equation: MPC=102−(23.45×lnV); wherein V is the velocity or flow rate of the fluid in the system, i.e., the fluid subjected to ultraviolet radiation. Once the MPC has been removed, a desired fluid flow rate can be established that allows for successful treatment with a disinfecting amount of ultraviolet radiation. For example, for fluids treated at a flow rate of about 5 gallons per minute (GPM) in a ¾" diameter tube, MPC removal should be at least about 50% (102−(23.45×ln5)=50%). For a fluid treated at a flow rate of about 40 GPM, MPC removal should be at least about 2.5% (102−(23.45×ln40)=2.5%). Flow rates are typically from less than about 1 to about 150 GPM or more, and preferably from about 10 to about 60 GPM. However, as fluid flow rates are controllable, the disinfection process can be tailored to the working parameters of most any configuration of machines. Using this simple formula, fluid disinfection by ultraviolet radiation can be successfully predicted and accomplished at almost any flow rate.

The principal contaminants in a contaminated fluid such as, for example, an industrial fluid, are heavy oils including way oils. Although solid particles may be present, MPC is a volume percentage, not a weight percentage and particle removal is not considered in the calculation. Consequently, MPC is a calculation of the volume of oil that must be removed from the fluid for successful disinfection by ultraviolet radiation in a flowing system. Nevertheless, with many types of fluids, particle removal may be required as there can be a synergistic effect of certain metallic particles with heavy oils that rapidly leads to UV occlusion of most any surface. In such cases only when both heavy oils and metallic particles are removed can occlusion be prevented and radiation treatment be successful.

Many contaminating oils have differing viscosities that can be significantly different from the viscosity of the uncontaminated fluid being treated. This viscosity difference can be taken into account when calculating MPC or minimum flow rate (MFR). Way oils tend to be fairly viscous with viscosity measurement of between about 160 to about 1150 Saybolt SUS at 100° F. Cutting oils and pretreating oils have a lesser viscosity of from about 41 to about 199 Saybolt SUS at 100° F. Hydraulic oils are of middle viscosity of from about 63 to about 147 Saybolt SUS at 100° F. The effect of increasing viscosity of contaminant oil from a mean viscosity of 275 Saybolt SUS at 100° F. for medium viscosity contaminant oils, such as hydraulic oils, to a mean of 665 Saybolt SUS at 100° F. for heavy contaminant oils such as way oils, is to increase the requirement for removal of contaminant oils be about 10%. In a similar fashion, when the viscosity decreases to a mean light oil level of 120 Saybolt SUS at 100° F., the amount of oil to be removed decreases by about 10%.

Fluids that can be disinfected according to the invention include, for example, liquids such as water and flavored water, carbonated beverages and other fluids under pressure, flavored drinks, fruit juices, soft drinks, beers, wines, liquors and industrial fluids. Industrial fluids are fluids typically used in assembly lines and other manufacturing configurations, to cool, clean and lubricate as appropriate to the specific operation being performed. Typical industrial fluids accumulate about 1% to 7% hydrophobic hydrocarbon contaminants, with the remainder of contaminants being silicon oils and soluble lubricants, all usually in an aqueous medium (e.g. water). However, non-aqueous fluids, such as electro-discharge machine fluid (EDM), can also be successfully disinfected by the practice of this invention. Preferably, fluids to be disinfected are substantially opaque. Substantially opaque fluids are fluids that do not allow lethal ultraviolet radiation energy to pass more than about 1.5 mm into the fluid.

In large factories, manufacturing lines can be quite long and contain huge volumes of fluid such as in the manufacture of automobiles, aircraft and automobile and aircraft parts. These lines comprise one or a plurality of machines in series (i.e. a working line), a fluid reservoir or tank, a plumbing system interconnecting the various machines and often a fluid sump with a pumping mechanism. The sizes of the tubes that guide the flow of the fluids in such system vary tremendously depending on the location in the system ranging from small to large. Smaller tubes may have a diameter of greater than about 4 mm, greater than about 6 mm, or greater than about 10 mm or more. Larger tube sizes, greater than two inches, greater than three inches and even greater than four inches, are typical in most industrial settings. As the invention is not limited by the ability of UV radiation to penetrate a fluid, most all fluids used in industrial systems can be treated according to the methods of the invention.

Specific types of fluids typically found within these manufacturing lines include metal-working fluids, machine-tool coolants, machine-tool lubricants, electro-discharge machine fluid, Zyglo, electro-coating fluid, chassis-washing fluid, top-coating fluids, sonic-bath fluids, spot- and steam-welding coolants, electron-beam and laser-welding coolants, test-cell waters for metal processing, plastic molding and forming coolants, quenching fluids, recycled and recirculation fluids, and combinations thereof.

In the disinfection of fluids, one or more prefilters or particle filters are typically used to remove heavy particles such as metallic or plastic chips and filings. With industrial coolants, this step removes metallic particles which, in combination with way oils, lead to sludge formation and subsequent occlusion of UV transmissible tubing or UV lamps in the system. Prefilters are preferably comprised of metal or plastic strainers that remove the larger and coarser particles present in the fluid (e.g. metallic or plastic particles, chips and shavings). Additional filters that can be used include composite fiber-mesh filters and the like. Mesh filters contain fibers of, for example, polyester, polypropylene, nylon, Teflon, Nomex, Viscose or combinations of these materials. These fibers have a wide variety of pore sizes (e.g. 2, 5, 10, 15, 20, 25, 30, 35, 40, 45, 50, 75, 100, 125, 150, 175, 200, 300, 400, 500 micron) and are commercially available.

Once larger particles have been removed, fluid flows to a second stage filter such as, for example, a coalescent filter to remove additional contaminants. Coalescent filters contain fibers, structured with various pore sizes, that are adherent to the contaminant. Coalescent filters are commercially available that are adherent, for example, to the heavy way and hydraulic oils, such as tramp oils, common in industrial fluids. For industrial fluids, the combination of a particle filter and a separator, such as an oil separator, removes sufficient amounts of contaminant particles and oils present in the coolant to allow for successful disinfection with ultraviolet radiation. An important advantage of this combination is that both live and dead bacteria are removed from the fluid which thereby reduces the requirement for the ultraviolet system to conduct all of the killing and at the same time. As dead bacteria are an important nutrient source for bacterial growth, removal of dead microbes is an important and previously unrecognized advantage.

In this embodiment of the invention, fluid flows from the separation system to the disinfection system. After establishing a fluid flow rate sufficient to scour the ultraviolet lamps or UV transmissible tubing and, if necessary, removing excess contaminating oils, fluid is disinfected by treatment with ultraviolet radiation. Radiation may be applied from ultraviolet lamps submerged within the fluid or kept separated from the fluid. Submerged lamps generally require protection from the fluid such as a quartz jacket or coating that allows for a high transfer of UV radiation while preventing damage to the UV lamps. Preferably, the disinfection system is a dry system where the UV lamps are placed in close proximity to, but not within the fluid. This allows for easy UV lamp replacement and heat generated from the UV lamps can be disseminated without damaging the fluid. A dry system requires infrequent maintenance, a real advantage for this design. In one embodiment of the invention, ultraviolet treatment is applied at greater than about 12,000 microwatt seconds per $cm^2$ of radiation, preferably greater than about 20,000 microwatt seconds per $cm^2$, and more preferably greater than about 40,000 microwatt seconds per $cm^2$. In the absence of a minimum amount of contaminants, as determined by flow speeds, fluid can be successfully exposed to the killing effects of ultraviolet radiation.

The invention possess many advantages. As ultraviolet radiation neither adds to nor detracts anything from the fluid, the process has no effect on the integrity of the fluid. A need for chemicals such as germicides and biocides, presently used in the disinfectant of fluids, is greatly reduced or completely eliminated. As biocides are themselves expensive and pose serious health risks to workers, the savings can be considerable. In addition, many chemicals are detrimental to the efficiency and integrity of the fluid. Consequently, use of the methods and apparatus of the invention greatly extends the useful life and/or shelf-life of the fluid. In addition, odors from contaminated fluid and some biocides can be fairly unpleasant. Use of the invention also reduces or eliminates such odors providing an improved air quality and working environment.

Using the process and apparatus of the invention, bacteria counts acceptable to federal (e.g. EPA or FDA), state or local regulations and various other health fields can be set for a particular fluid. This process allows for the possibility of multiple passes with resident time in the UV system of exposure for seconds or minutes. For example, in one test using industrial fluid, a bacteria count before coolant was processed through the oil separator and UV unit was approximately $10^3$ to $10^6$ microorganisms per ml. After a 24 hour cycle, the microorganisms count was almost zero. With this process, costs for the disposal of contaminated coolants and for coolant replacement are substantially reduced. In addition, chemical pollution to the environment is minimized or can be avoided where processes are available for recycling used fluids. In addition, microbial counts following UV treatment of substantially opaque fluids can be further reduced by introducing turbulence to the fluid flow path thereby bringing bacteria to the fluid surface for greater killing exposure.

The methods and apparatus of the invention can be used in both closed and open systems. In closed systems, such as both large and small scale assembly lines and other manufacturing lines, fluids such as coolants flow down the line to cool and lubricate machine tools. Coolants are heat transfer mediums or thermofors and may be in liquid or a gaseous form having the property of absorbing heat from the environment and transferring that heat effectively away from the source. As such, coolants are used in the transportation industry, the tool manufacture industry and in most every small to large manufacturing plant. Coolants, as do most industrial fluids, come in a variety of colors such as gray, red, yellow, white, green and blue, and may be fairly thick in composition as compared to plain water. Types of coolants include propylene and ethylene glycol and Dowtherm. In addition, some coolants are anti-freezes such as, for example, propylene glycol.

In the assembly and manufacturing lines, coolants pick up a substantial amount of contaminants. Substantial means that the level of contaminants are increased so as to shorten the normal useful life of the fluid due to their concentration and interference with coolant function and to the presence of an enhanced environment for microbial growth. Particles such as metallic or plastic filings or iron or steel chips, typically accumulate on and in the machines being cooled. Particles such as microorganisms, insects, insect parts and other debris also collect in the reservoir and in the lines. These particles are all swept-up in the fluid flow. Other contaminants include lubricating oils, pretreating oils, hydraulic fluids and way oils. Lubricating oils have a low viscosity and, compared to way oils which are quite viscous, and fairly thin (i.e. heavy oils and oils with long carbon chains). Tramp oils (i.e. renegade contaminant oil that gets into machine operations), typically considered a type of way oil also accumulate in the fluid, as well as water which accumulates from condensation in the lines. These contaminant substances are sticky, adhere to the walls of pipes and the UV system components, and further encourage microbial growth, especially bacterial growth in the line and in the fluid reservoir. Such substances also bind bacteria to their molecular interface surfaces. Preferably, these bacteria are removed during a physical separation step thereby reducing the requirement of the ultraviolet to be the sole bacterial control mechanism.

In the disinfection process, coolant is subjected to filtration by passing the coolant through a prefilter to remove larger particles and debris. The prefiltered fluid is passed through a first stage filter that removes finer particulate matter. Such filters remove particles of greater than about 100 microns, preferably greater than about 50 microns, more preferably greater than about 25 microns and still more preferably greater than about 10 microns. Other contaminants, such as way and other tramp oils are removed using one or more oil separators which are, preferably, dedicated to the removal of such contaminants.

Many techniques for the removal of oil from a continuous or running stream of fluid are well-known to those of ordinary skill in the art. For example, at least most of the oil can be removed from a fluid by passing the fluid through a plurality of oil separators. Preferable, one of such oil separators is a coalescent filter. Coalescent filters comprise fibers with predefined pore sizes wherein the fibers are adherent to the contaminants. Such filters are commercially available (U.F. Strainrite, Inc; Lewiston Me.). Other oil separators useful according to the methods of the invention include oil skimmers and density centrifuges. Preferably, the pretreatment steps include a strainer step to remove particles of greater than about 100 microns, a centrifugation step to remove a large portion of the heavy oil contaminants, a prefilter step to remove contaminants of greater than about 25 microns, and a coalescent filter for removal of oil and small contaminants.

Once less than a specified level of contaminants has been reached, the contaminant-reduced fluid can be successfully irradiating with a disinfecting amount of ultraviolet radiation such that any contaminants that remain do not interfere with disinfection of the coolant. The disinfecting amount of radiation depends on the flow rate and volume of the fluid being treated at any one moment. For most applications, radiation is administered at from at least about 15,000 microwatt seconds/cm$^2$ or more, depending also on the type of ultraviolet lamps, the ultraviolet transmissibility of the tubing, the orientation of lamps around the fluid-filled tubes and the structure of the tubing (e.g. flat verses rounded). As the UV lamps can be separated from the fluid, the method is preferably a dry disinfecting system. Although generally not required or necessary, it is also possible to sterilize a fluid by increasing the amount of ultraviolet radiation administered. Ordinarily, though, sterilization is not required to maintain a safe and workable cooling system.

The oil separator and the ultraviolet radiation generating system can be designed as modular units to further increase convenience and to reduce overall costs. As such, the system can be operated continuously, subject to periodic maintenance for UV lamp changes or removal of accumulated contaminants, for a period of greater than one week, greater that one month, greater than one year or even longer.

All types of conventional radiation treatment can be administered to the contaminant-reduced fluid including treatment methods described in U.S. Pat. No. 4,798,702, for use of corrugated ultraviolet-transmissible tubing, U.S. Pat. Nos. 4,971,687 and 4,968,891, for use of thin films, U.S. Pat. No. 5,494,585 for use of a cavitation process, and U.S. Pat. Nos. 3,527,940 and 4,766,312, for maximizing radiation treatment by passing fluids through a helical path. In addition, such radiation can include ionizing radiation, such as gamma radiation or x-rays in place of ultraviolet. Thin films may be shaped by the structure of a portion of the ultraviolet transmissible tube. The fluid may be guided into a thin film with a thickness of less than about 5 mm, preferably less than about 4 mm, and more preferably less than about 2 mm. As radiation of substantially opaque fluids can disinfect about 1 mm to about 1.5 mm of fluid, radiation transmitted from all sides of a 2 mm to 3 mm fluid flow can be disinfected. Where complete sterilization of the fluid is desired, thin films may be useful. A wide variety of ultraviolet sterilization devices or self-contained units can be used with one or a plurality of ultraviolet lamps both within, between and surrounding the tubing.

Figure 2A:
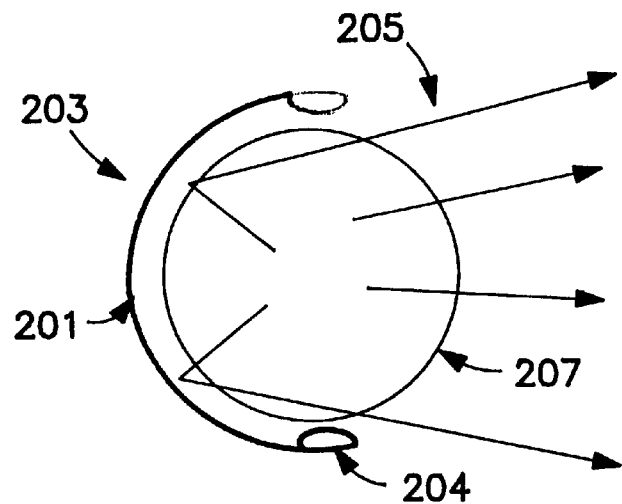
FIG. 2 Reflector designs for optimizing UV reflection (A) in a single direction and (B) in nearly 360° of reflection.
Figure 2B:
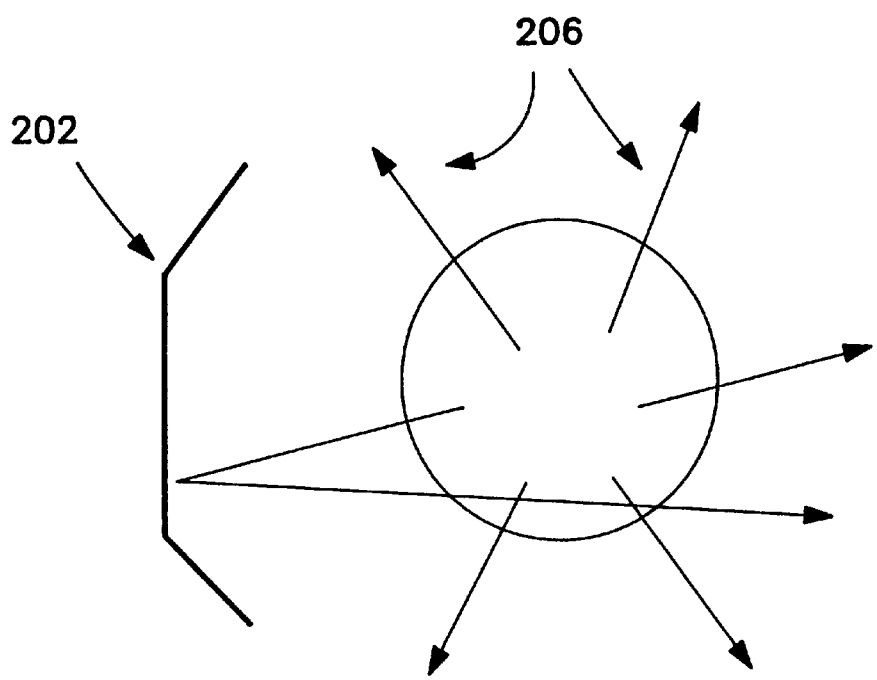

Tubing and thus fluid exposure to the radiation can be optimized by creating an orientation pattern of UV lamps around the tubing with ultraviolet reflective surfaces directing the radiation toward the fluid (FIG. 1). Radiation exposure is highest at the fluid-surface interface. Disinfection units placed within containers can be coated on the interior surfaces of housing 101 with reflective substances. One or more UV lamps 103 and reflectors 102 can be positioned so as to maximize exposure of the fluid in tube 104 to the available radiation. Reflectors can be coated with an ultraviolet reflective material such as, for example, an aluminum, a titanium or titanium nitrate based material, or a combination thereof. Preferably, the reflector is coated by a sputtering process whereby the coating material is deposited in a vacuum onto a solid support such as an aluminum or teflon surface. In addition, UV lamps may be partially coated with UV reflector substances or UV blocking substances to direct energy output and/or prevent exposure of other surfaces to UV radiation. Two types of reflection techniques are shown in FIG. 2. In FIG. 2, reflectors 201 and 202 are position in close proximity to UV lamp 207. The reflector of FIG. 2A comprises UV and heat resistant plastic reflector 203 to which is applied an aluminum coating by sputtering and retainer bump 204 at each end of the reflector which serves to fix the reflector to the UV lamp. According to these designs, ultraviolet reflections 205 and 206 can be maximally directed to the fluid.

Many types of reflectors are known to those of ordinary skill including polished aluminum reflectors, described in U.S. Pat. No. 4,534,282, reflectors mounted to the frame, described in U.S. Pat. No. 3,634,025, elongated curved reflectors, described in U.S. Pat. No. 4,766,321 and outward reflecting reflectors.

As known to those of ordinary skill in the art, ultraviolet radiation can be directed to kill eukaryotic cells, bacterial cells, fungi and spores, virus particles and almost any living microorganism. Based on the intensity of the radiation treatment, one of ordinary skill can choose to disinfect or completely sterilize the fluid. Sterilization is usually unnecessary for industrial fluids, but is often required to meet EPA or FDA guidelines for products regulated by government guidelines such as pharmaceuticals and animal products.

Industrial fluids, for example, typically contain between about $10^5$ to about $10^9$ bacterial per ml. Reduction of bacterial levels to at or less than about $10^3$ is generally required to provide a safe and risk-free working environment as well as to extend coolant life. Treatment of contaminated fluid, according to the methods of the invention, kills greater than 90% of the microorganisms in the contaminated fluid, preferably greater than 95%, and more preferably greater than 99%. This reduces the bacterial load of the fluid at least about one log, preferably at least about 2 logs, more preferably at least about 3 logs. Increased disinfection is possible to decrease the bacterial load of the fluid at least about 4 logs, preferably at least about 5 logs, and more preferably at least about 6 logs or more when necessary. Treatment times vary depending on the volume of fluid being treated and the amount of contamination and the rate of fluid flow. Therefore, treatment may be performed, for example, in a continuous system operated for months, weeks, days or hours to reduce the bacterial load to desired levels and to maintain such levels.

Another embodiment of the invention is directed to a method for disinfecting a contaminated fluid flowing through a tubing system. According to this method, at least a minimum flow rate (MFR) is established that prevents occlusion of the inner surfaces of the tubing and, preferably, those portions of the tubing that are UV transmissible. As the fluid passes through the UV transmissible portions, the fluid is irradiated with a disinfecting amount of ultraviolet radiation. The minimum flow rate can be calculated from the level of contaminants in the contaminated fluid according to the equation: $MFR = e^{((102-PC)/23.45)}$; wherein PC is the percentage of contaminants in the contaminated fluid. Preferably, contaminants included in the calculation of PC are those contaminants which are in a liquid state and not solids such as particulate matter. For example, a contaminated industrial fluid will typically contain a variable percentage of contaminating oil and an amount of solid particles. Only the volume percentage of oil would be used to determine the value for PC. From this value, the minimum flow rate that would prevent occlusion can be determined. However, as the percentage of contaminants in the contaminated fluid can be adjusted, the flow rate needed to prevent occlusion can also be adjusted. This would be useful in those instances wherein the level of contaminants would be so high so as to require a flow rate that would be impractical for the particular system. In such cases, some percentage of the contaminants can be removed and the flow rate reduced according to the equation. Upon removal of sufficient contaminating oil, a workable flow rate can be established.

Another embodiment of the invention is directed to a method for disinfecting a fluid comprising establishing a turbulence in a fluid stream during irradiation. As ultraviolet radiation cannot pass more than about 1 mm to about 2 mm into most opaque fluids, it is important to maximize exposure of the microorganisms in the fluid to ultraviolet radiation. As fluid travels transversely as in a turbulent or non-laminar manner to fluid flow in the tubing, there is a greater likelihood that the microorganisms in the fluid will be subjected to ultraviolet treatment. Turbulence should be sufficient to provide a Reynolds number greater than that defining a laminar flow or greater than about 4,000. By encouraging microorganisms to move transversely, microbes are brought to the surface of the fluid at the inner surface of UV-transmissible tubing 104 and not hidden within mid-sections of the tube. Passage of fluid and microorganisms within the fluid are moved from zones of no or low UV radiation to surface zones of high UV radiation. In this manner not only is killing effect magnified, but the turbulence creates a scouring effect within the tubing. Radiation can also induce oxidation of certain chemicals that may be present in the fluid which may add to both the scouring and killing effects.

Tube sizes that guide the flow of turbulent fluid are not limited by the ability of UV radiation to penetrate the fluid. Tube diameters which can be utilized for this method may have a diameter of greater than about 4 mm, preferably greater than about 6 mm, and more preferably greater than about 10 mm or more. Tube sizes of greater than two inches, greater than three inches and even greater than four inches, typical in most industrial settings, are also applicable to this method.

Figure 3:
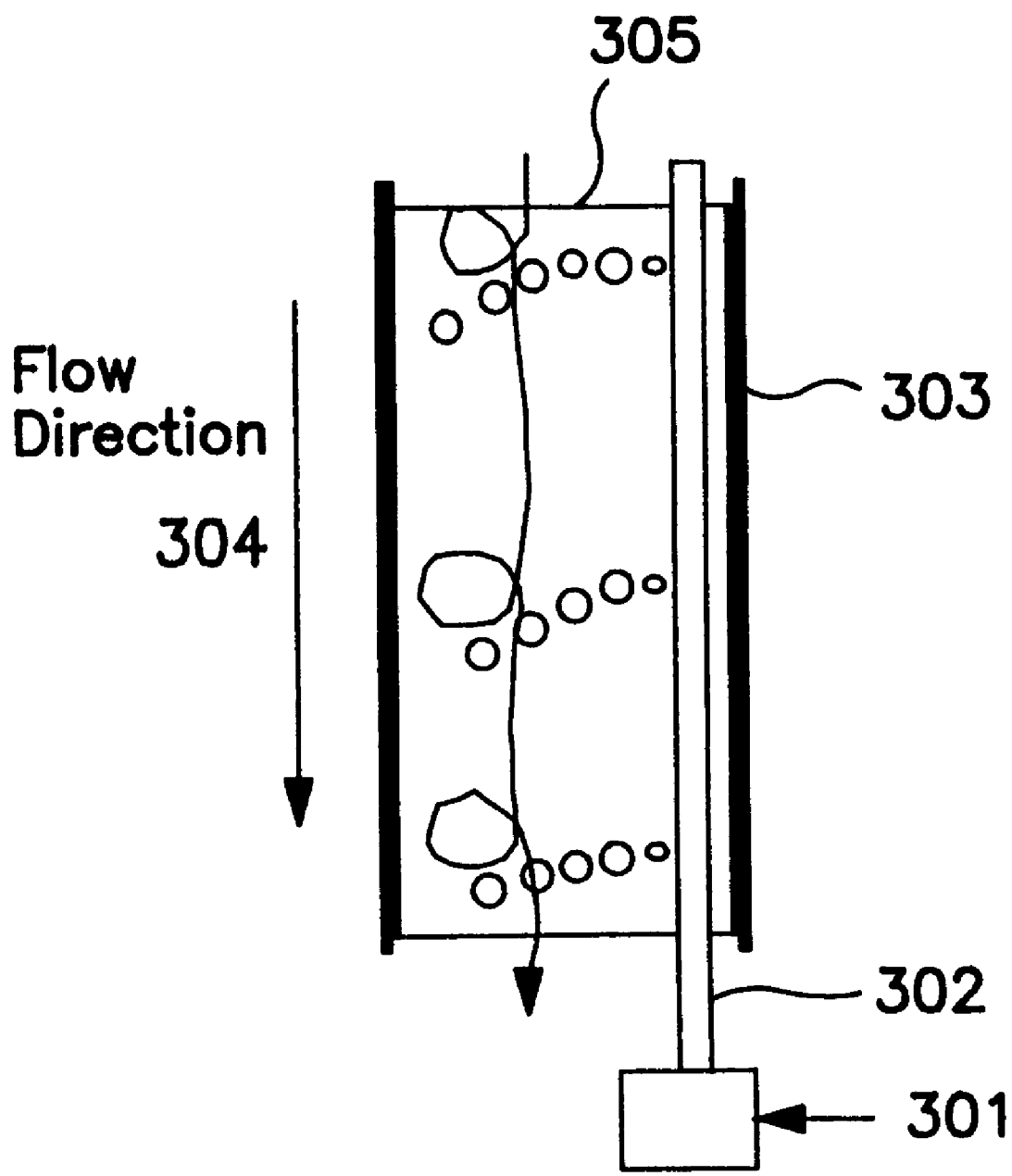
FIG. 3 Tube within a tube turbulence-generating mechanism.

Turbulence-generating systems that encourage transverse motion include aeration systems that create gaseous bubbles within the tube. As shown in FIG. 3, air pump 301 pumps air into inner tube 302 which contains a large number of small holes 303. These holes allow the pressurized gas to escape from tube and generate fluid turbulence, transverse to fluid flow direction 304, within the lumen of the tube 305. Preferably, the gas does not interact with the fluid components. Typical gasses that can be used for most fluids include, for example, air, carbon dioxide, oxygen, hydrogen helium, nitrogen, argon and combinations of gasses, any of which may be pressurized. In addition, this technique is not limited to gas. Liquids may be forced into the inner tube as well creating turbulence in the fluid as the liquid exits holes within the inner tubing walls. Liquids which can be used include the liquid itself, which may be the contaminated liquid or liquid that has been treated according to the invention, an inert liquid or another liquid that does not negatively interact with the fluid being treated. The tube within a tube configuration preferably has a controllable pressure differential within the tubing.

Figure 4A:
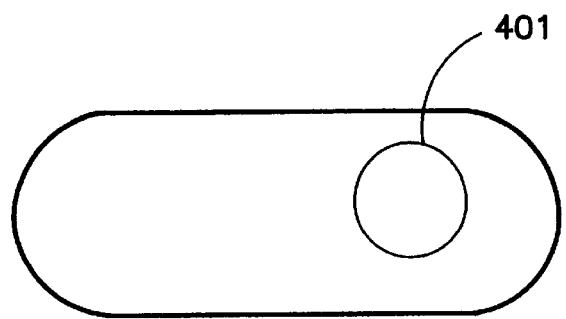
FIG. 4 (A) Single bead and (B) beads on a string turbulence-generating mechanisms. (C) Cross-sectional view of a UV transmissible tube.
Figure 4B:
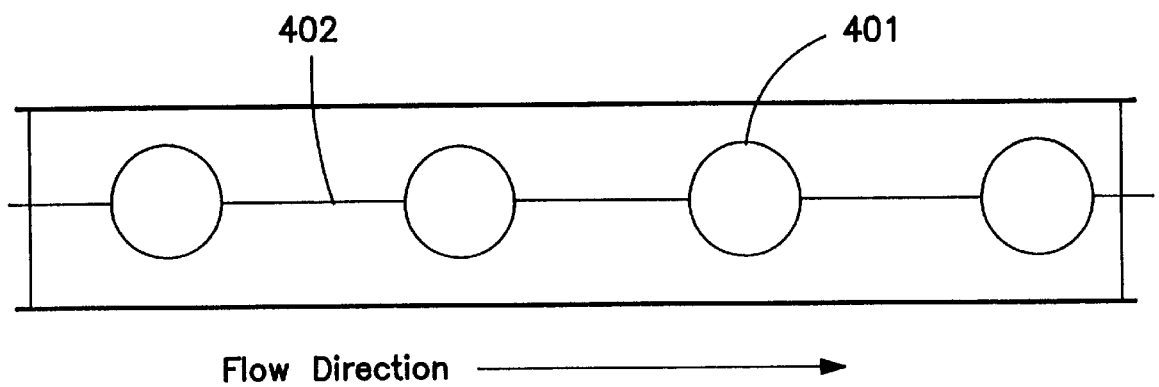

Turbulence can also be generated by suspending articles within the fluid stream such as, for example, ridges, helical vanes, impellers, baffles, projections, vanes, paddles, wheels, beads, cones or slotted cones, or almost any geometric structure. Such structures or turbulators or agitators may be on a string, free in the fluid or free, but confined in a section of the tubing. As shown in FIGS. 4A and 4B, bead 401 can be attached to string 402, which may be constructed of a metal such as steel or a composite polymer, and is shown both longitudinally and in cross-section. The beaded string is placed into the lumen of a tube along the direction of fluid flow. As fluid impacts the bead, fluid is directed transversely or turbulently to the sides of the tube where ultraviolet radiation exposure is maximized. As shown in FIG. 4, bead 401 is slightly smaller than the lumen of the tube. However, a variety of sizes may be utilized the only requirement being that they fit within the lumen and not cause an impractical or high head pressure in the system. Combinations of these techniques may also be utilized.

Another embodiment of the invention is directed to combinations of fluid disinfection treatments such as those described above. Fluids may be treated with a combination of contaminant removal and turbulence generation followed by radiation treatments. Such treatments may be further supplemented with conventional treatments such as, for example, filtration, centrifugation and the addition of biocides including anti-bacterial and anti-fungal agents. However, as the combination is highly effective, the amount of biocidal agents that are added can be greatly reduced as compared to conventional methods. The working environment would be improved due, in part, to the lack of noxious fumes caused by microbe-induced decaying fluid, and the lack of biocides and/or microorganisms, greatly improving air quality. Health risks to workers are also greatly reduced.

Another embodiment of the invention is directed to an apparatus for disinfecting an industrial fluid. The apparatus comprises a tubing system, an ultraviolet radiation-treatment system, a turbulence-generating system and/or a contaminant-separation system which, for example, may be specific for particles, microbes, oil or a combination of these contaminants.

Figure 4C:
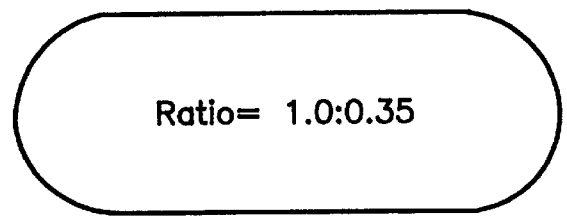

In a dry modular apparatus, the tubing system guides the passage of the industrial fluid at a determinable flow rate through the apparatus with the UV lamps separated from the fluid. Tubing of the system is composed of ultraviolet-transmissible material such as, for example, a fluoropolymer, as described in U.S. Pat. No. 4,798,702. Tubing which is useful for the tubing system should preferably be capable of withstanding pressures of greater than about 70 psi, and preferably greater than 150 psi, have a thickness of between about 20 to about 80, and more preferably 60, thousandths of an inch, and be transmissible to greater than 90% of the ultraviolet radiation being applied. A preferred type of tubing has been identified and is composed of tetrafluoroethylene-perfluoro (propyl vinyl ether) copolymer or, alternatively, perfluoroalkoxy polymer (Zeus Industrial Products, Inc.; Orangeburg, S.C.) and fluorinated ethylene propylene (FEP) (Product No. 3E 750 SW 0; Zeus Industrial Products, Inc.; Orangeburg, N.C.). These types of tubing are resistant to fouling, have a high corrosion resistance, are both strong and light weight, and are highly UV transmissible with transmission factors of greater than about 95%. Preferably, the tubing is flatted or oval shaped with a cross-sectional diameter ratio of about 1 to about 0.35, as shown in FIG. 4C. Surface area exposed to UV radiation is increased and the surface area of tubing shadowed by adjacent coils of the same spiral or by the coiled lengths of tubing is minimized. The flatted surface may be modified to increase the wetted surface area by incorporation of longitudinal serrations, coarse serrations or waves. These modifications increase UV effectiveness by increasing the area of the fluid exposed to the UV.

The tubing system may also comprise one or more inlet and outlet ports attached to opposite ends of a coiled tube. The inlet ports allow for the flow of fluid from the line or the reservoir into the disinfection unit. The outlet port allows for the flow of disinfected fluid back to the line such as a manufacturing or assembly line. Tube surfaces may be smooth, furrowed, wrinkled, indented, transverse ridged or corrugated, and the tubing may be coiled, parallel, twisted, serpentine or in a helix at the point of radiation treatment. Ultraviolet lamps can be positioned outside and inside the tubing configuration as well as between the tubes. Tubing has a flattened to rounded cross section (e.g. oval). However, the system may be configured to create a thin film of fluid (flattened) at the point of radiation treatment to maximize radiation exposure.

The contaminant separation system should be designed to remove particulate and other contaminants from the fluid. Particulate matter can be removed with filters having pore sizes designed to remove particles of greater than 100 micron, preferably greater than 50 micron, and more preferably greater than about 10 micron. The contaminant separation system contains an oil separator which is designed to remove at least most of the oil from the fluid. Examples of suitable types of oil separators include skimmers, centrifuges and coalescent separators. Other unwanted liquids can be removed by a separation means particular to the type of liquid. Such separation means are known to those of ordinary skill in the art.

In addition to a contaminant separation system, the apparatus also includes an ultraviolet radiation system. The radiation system is comprised of one or more ultraviolet lamps in close proximity to the tubing system. As the lamps do not come into direct contact with the fluid, the apparatus may be described as a dry system (i.e. the lamp does not come into direct contact with the fluid contained within the UV-transmissible tube). In a dry system, fluid components are not subjected to unwanted heating from the UV lamps. Further, the UV lamps are not cooled by circulating fluid and, therefore, maintain a temperature high enough for optimum generation of UV radiation. Also, maintenance of lamps is minimized due to the separation of dirty or contaminated fluid from the lamp surfaces. Preferably, there are a plurality of ultraviolet lamps surrounding a coiled tube on both the inside and outside, and even between, the coils. As the energy imparted to the target fluid is proportional to the square of the distance of the UV lamps to the fluid, that distance should be minimized to maximize the amount of energy transmitted to the fluid. The unit can be ventilated or air conditioned to prevent heat build-up as necessary to prolong the life of the UV lamps and so as not to damage the fluid.

The apparatus may also contain a turbulence-generating system to maximize exposure of the fluid to the radiation. The turbulence-generating system should preferably be placed into the tubing wherein the fluid is exposed to the radiation. Examples of turbulence-generating systems include structures attached to the walls of the tube or otherwise free-floating in specified areas of the lumen of the tube. Such structures include nearly any shaped article such as paddles, beads, cones, vanes, ribbons and the like, any of which may be slotted, and which may be fixed to tubing walls, attached to each other or attached to a string and suspended in the fluid. Fixed structures may be placed at set angles to the laminar flow of the fluid, preferably up to about 90°, such as, for example, about 20°, about 30°, about 45°, about 60° or about 75°. Other turbulence-generating systems include tube within a tube configurations that allow for a pressure differential, ultrasonic vibrations, split-flow systems or aeration within the fluid. The apparatus may also contain circuitry appropriate for proper monitoring and control of all aspects of the apparatus. The additional of computer control can also be utilized to create units that are completely or partially automated.

Figure 5:
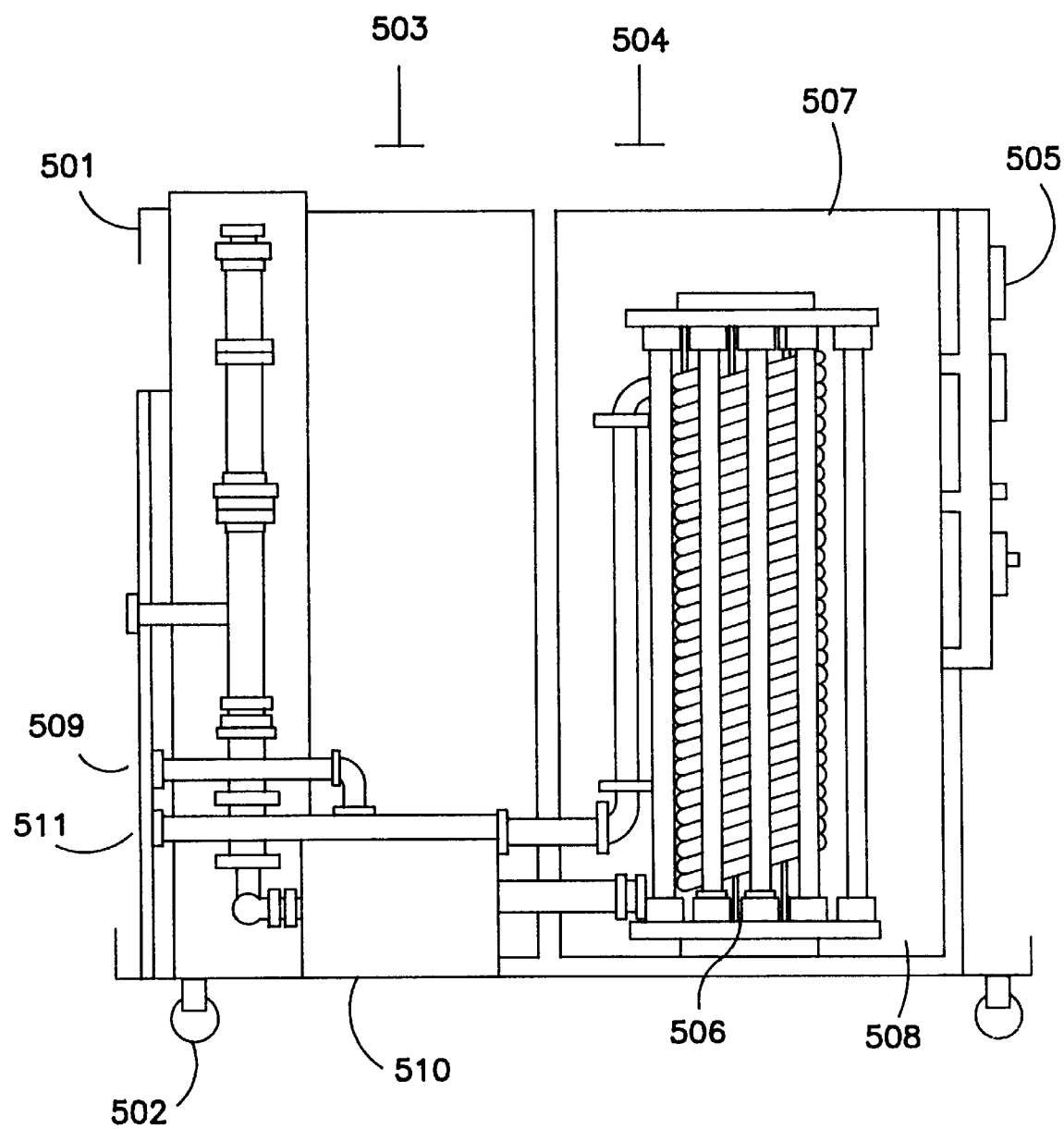
FIG. 5 The L02C filtration and germicidal system.

An example of one embodiment of the apparatus is shown in FIG. 5. As shown, the apparatus is contained within housing 501 which is on casters 502 and, consequently, quite mobile. The basic unit contains pump and oil separator module 503, ultraviolet module 504 and electronics module 505 which may contain a fan, gauges reporting on the condition of the unit and/or the status of the fluid flow, indicator lamps and switches. UV lamps 506 are positioned around a helical portion of tubing 507 to maximize UV exposure. Reflectors 508 are positioned around UV lamps 506. Fluid enters through inlet port 509, travels through oil separator 510, tubing 507 and, disinfected, exits through outlet port 511. As the unit is dry modular in design, it can be used to disinfect many different types of fluids.

According to one embodiment of the general process, coolant to be disinfected is first treated by passing through a screen to remove metallic particles and other debris. Coolant is next run through an on site commercial centrifuge to reduce contaminant concentrations to approximately two percent. Coolant to be treated is drawn into the system by a pump mechanism. The pump forces coolant into a filter vessel under pressure which contains a filter cartridge. The cartridge will normally contain a 10 to 20 micrometer pore size which facilitates separation of the oil and binding of the oil to the fiber structure of the cartridge. Such filtration performs the important role of removing large amounts of both living and dead bacteria. Removal of the dead bacteria reduces nutrient loading in the fluid. The differential pressure between the input and the output of the filter vessel is used to monitor the condition of the filter cartridge and can be read at the electronic module. When the pressure reaches the specified differential, in most cases the greatest differential, the filter cartridge has filled with contaminant oil and must be replaced. Rate of oil accumulation will vary depending upon the amount of oil in the coolant and the viscosity of the oil as well as the type of coolant. The fluid is forced under pressure into germicidal module 507 and disinfected before being discharged from outlet 511.

Another embodiment of the invention is directed to fluids treated according to the methods of the invention. Such fluids includes liquid which, after treatment, are substantially free of microbial contamination and, optionally, other contaminants as well as way and tramp oils, microbial particles and other particulate materials. Substantially free means that the population level of microbes has been reduced to a level that does not pose a risk to workers, resulting in an improved quality to the working environment. Such fluids include machine tool coolants, machine tool lubricants, electro-discharge machine fluid, Zyglo, electro-coating fluid, chassis-washing fluid, top-coating fluids, sonic-bath fluids, spot- and steam-welding coolants, electron-beam and laser-welding coolants, test-cell waters for metal processing, plastic molding and forming coolants, quenching fluids, recycled and recirculation fluids and combinations thereof. Other fluids including water such as potable water, water to be consumed in areas of suspected contamination, water supplies from natural or man-made emergencies, water used during military operations, third-world water supplies, livestock water and beverages such as, for example, flavored and plain water, flavored drinks and drink blends, vegetable, fruit and other juices, soft drinks, beer, wine and other liquors.

The following examples illustrate embodiments of the invention, but should not be viewed as limiting the scope of the invention.

EXAMPLES

Example 1
The Prototype Filtration/Germicidal System

A novel process has been discovered to treat coolant fluids with a combination of filtration and ultraviolet (UV) light exposure. This process has the ability to disinfect both opaque and transparent industrial coolant fluids and may eliminate or reduce the need of biocide treatments for microbial control. This technology uses ultraviolet irradiation, a technique proven for the treatment of waste water effluent, which is effective against a wide range of microorganisms. The ability of the treatment to kill or control microorganisms under various operating conditions was determined.

The prototype filtration and germicidal system (FIG. 5) comprises two major operational modules, a variable-speed pump and filtering module (filter unit of module is a UF1 Filtration System; U.F. Strainrite, Inc., Lewiston, Me.) and a germicidal module. In operation, about 15 to about 20 gallons of fluids are required to fill the filtration module, and the filtering module has a minimum capacity or flow rate of about six gallons per minute. The pump and filtering module and the germicidal module are controlled from a separate control panel (the electronics module), attached to the side of the germicidal module. The ultraviolet output of the germicidal module can be adjusted by changing the number of ultraviolet generating lamps utilized. For these experiments, a maximum of 8 lamps were used although the module was also capable of lower UV output settings by using 2, 4, 6 or 8 lamps.

Example 2
The Prototype Test System

Approximately 45 gallons of used coolant, consisting of coolant concentrate diluted with water at a ratio of about 1 part concentrate to 3.5 parts water (22% oil and 78% water) was stored in a 50-gallon drum. This mixture was recycled through the L01 filtering unit and the majority of tramp oil and suspended particles were removed. After treatment, coolant in the reservoir was milky-white in color with almost unobservable tramp oil when visually inspected. Separated tramp oil was black in color. About three gallons of tramp oil were extracted from the used coolant. Bacterial colony forming units (CFUs) were enumerated using Sani-Check BF paddles (Biosan Laboratories, Inc.; Warren, Mich.) and the results are shown in Table 1.

TABLE 1

Bacterial Colony Counts

| Sample size | Count (CFU) | Concentration (CFU/ml) |
| --- | --- | --- |
| Untreated coolant reservoir | $10^7$–$10^8$ | $2 \times 10^8$–$2 \times 10^9$ |
| Tramp oil reservoir | $10^5$–$10^6$ | $2 \times 10^6$–$2 \times 10^7$ |
| Treated coolant before UV | 52 | $1 \times 10^4$ |
| Treated coolant after 5 min UV | 62 | $1 \times 10^3$ |
| Treated coolant after 15 min UV | 32 | $5 \times 10^3$ |
| Treated coolant after 30 min UV | 35 | $5 \times 10^3$ |
| Treated coolant after 60 min UV | 42 | $5 \times 10^3$ |
| Treated coolant after 120 min UV | 36 | $5 \times 10^3$ |
| Treated coolant after 180 min UV | 25 | $3 \times 10^3$ |
| Treated coolant reservoir after 180 min UV | 15 | $2 \times 10^3$ |

An important step in eliminating bacterial contaminants is the filtration and separation of tramp oil. The filtration module is capable not only of separating and removing tramp oil, but also of reducing the number of microorganisms present in used coolant. Tramp oil contains high concentration of dirt and contaminants.

After 15 minutes of treatment, a 50% reduction of bacterial count was achieved when microorganism counts obtained at the inlet-sampling port were compared to microorganism counts obtained in the outlet-sampling port. The bacterial population number remained the same for next 2 hours before a further drop was observed. After this period, bacterial populations resumed their decline. The drop in microbial counts continued in the coolant reservoir up to the end of the three hour experimental period.

Example 3
Testing of Model Unit L01 Using a Highly-Contaminated Coolant

Testing of Model L01 was performed at BioCheck Laboratories, Inc. (Toledo Ohio). Bacterial populations were monitored using membrane-filter and direct-plating technology as per Standard Methods (*Standards Methods for the Evaluation of Water and Waste Water* Vol. 19, published by American Public Health Assoc., 1994), and/or SaniCheck BF paddles (Biosan Laboratories, Inc.; Warren, Mich.). Trypticase soy agar (TSA) plates were used to monitor bacterial growth.

Samples were collected from the reservoirs and sampling ports. Bacterial counts were measured by diluting each sample tenfold with water and spreading a 50 µl aliquot of this dilution evenly over an 11 $cm^2$ surface (about 2.3 cm by about 4.8 cm). Test samples were maintained at room temperature for 48 hours before the results of bacterial growth were determined.

A first run was undertaken to determine the degree of bacterial survival in 25 gallons of highly contaminated used coolant during processing through the treatment unit at 10 gallons/minute (Run I). Coolant was dark green, opaque, with very little tramp oil or particulate matter. Initial inoculations of media paddles indicated that the coolant had more than $10^6$ CFU per ml of bacterial contamination.

Figure 6:
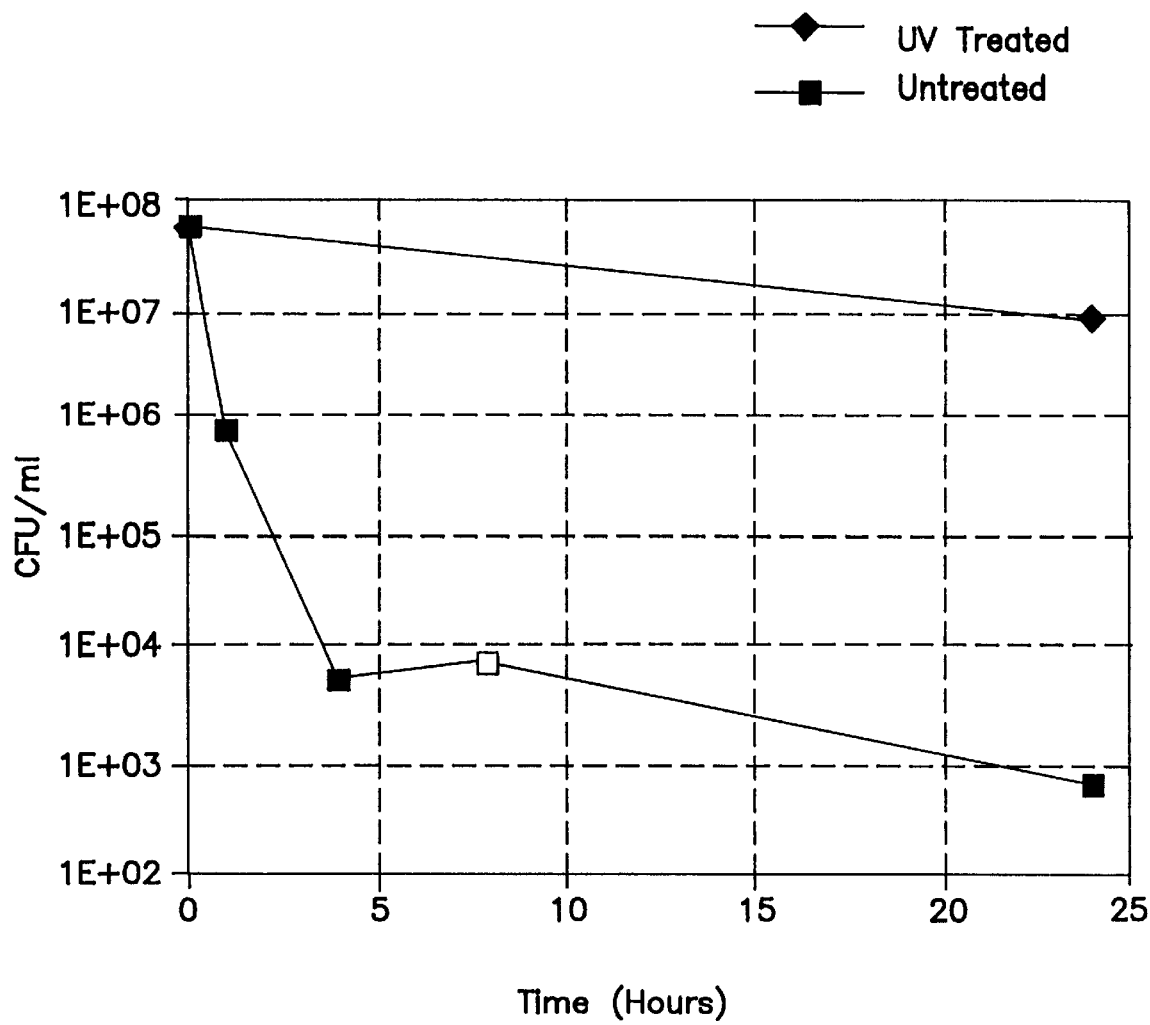
FIG. 6 Bacteriocidal effectiveness during UV treatment at 10 gallons per minute.

Results from the temperature monitoring and from membrane filtration/plate counting analysis of the coolant are shown in Tables 2 and 3, and FIG. 6. The number of bacteria cultured from the coolant in the recycling reservoir decreased over 100,000-fold during the 24 hour course of the treatment. While the most effective killing rate occurred within the first hour of treatment, continued treatment was effective in further reducing culturable bacterial numbers. Coolant was sampled and analyzed before it returned to the reservoir. The results indicated that approximately 90% of the bacteria in the coolant fluid were eliminated by a single passage through the coalescer filter and UV chamber.

TABLE 2

Results of Run I

| Time (minutes) | UV Chamber Temperature (° F.) | Coolant Temperature (° F.) |
| --- | --- | --- |
| 30 | 95 | 76 |
| 60 | 101.7 | 80 |
| 210 | 110.5 | 93.9 |
| 240 | 111.9 | 96.0 |
| 360 | 114.3 | 101.8 |
| 480 | 115.9 | 105.1 |
| 540 | 117.0 | — |
| 1440 | 115.9 | 108.7 |

Growth on media paddles also indicated that the filtration/UV treatment was highly effective in eliminating bacterial contamination of used coolant. Total volume was 25 gallons with a flow rate of 10 gallons per minute at 68.5° C. (Table 3). These results were very similar to those seen with membrane filtration/plate counting assays.

TABLE 3

Run I: Bacterial Population by Location

| Time (Minutes) | Sample Location | Total Gal. Treated | Bacteria (CFU/ml) | Bacteria (Paddle) |
| --- | --- | --- | --- | --- |
| 0 | Reservoir Post | 0 | 5.94E + 07 | 1E + 07 |
| 1 | Coalescer | 10 | 1.26E + 06 | — |
| 2 | Post UV | 20 | 8.99E + 05 | — |
| 60 | Reservoir | 600 | 7.47E + 05 | 1E + 06 |
| 240 | Reservoir | 2400 | 5.56E + 03 | 1E + 05 |
| 480 | Reservoir | 4800 | 7.42E + 03 | 1E + 05 |
| 1440 | Reservoir | 1440 | 7.47E + 02 | 1E + 03 |
| 1440 | Untreated | 0 | 8.69E + 06 | 1E + 07 |

These results indicate that the ultraviolet and oil separation treatments were very effective in eliminating bacteria in the fluid. From these data, a one hundred-fold drop was seen in the first hour. Another hundred-fold drop was observed over the next three hours. Bactericidal effectiveness continued at a reduced level between hours 4 and 8 of treatment. Finally, after 24 hours, the resulting bacterial number was reduced 100,000-fold compared to the original bacterial load. Total bacterial counts of untreated coolant bacteria decreased by approximately ten-fold over the 24 hour treatment period at 115° F.

The next run (Run II), focused on bacterial survival in used coolant during cycling through the apparatus at a flow rate of 40 gallons per minute. This run was designed to determine if the high level of bacterial killing observed in Run I could be maintained at the maximum flow rate obtainable with the L01 unit.

Temperature of the coolant in the reservoir and the temperature of the UV chamber were monitored during Run II. The temperature of the coolant increased during the course of the treatment (Table 4); however, throughout the test period, temperatures remained within operating parameters of the coolant.

TABLE 4

Run II: Operating Temperatures Over Time

| Time (Minutes) | UV Chamber Temperature (° F.) | Coolant Temperature (° F.) |
| --- | --- | --- |
| 0 | 69.5 | 69.5 |
| 3 | 84 | 70.4 |
| 30 | 93 | 73.8 |
| 60 | 98.8 | 77 |
| 120 | 103.8 | 82.9 |
| 150 | 105.3 | 86 |
| 240 | 108 | 92.3 |
| 480 | 111.4 | 101 |

Figure 7:
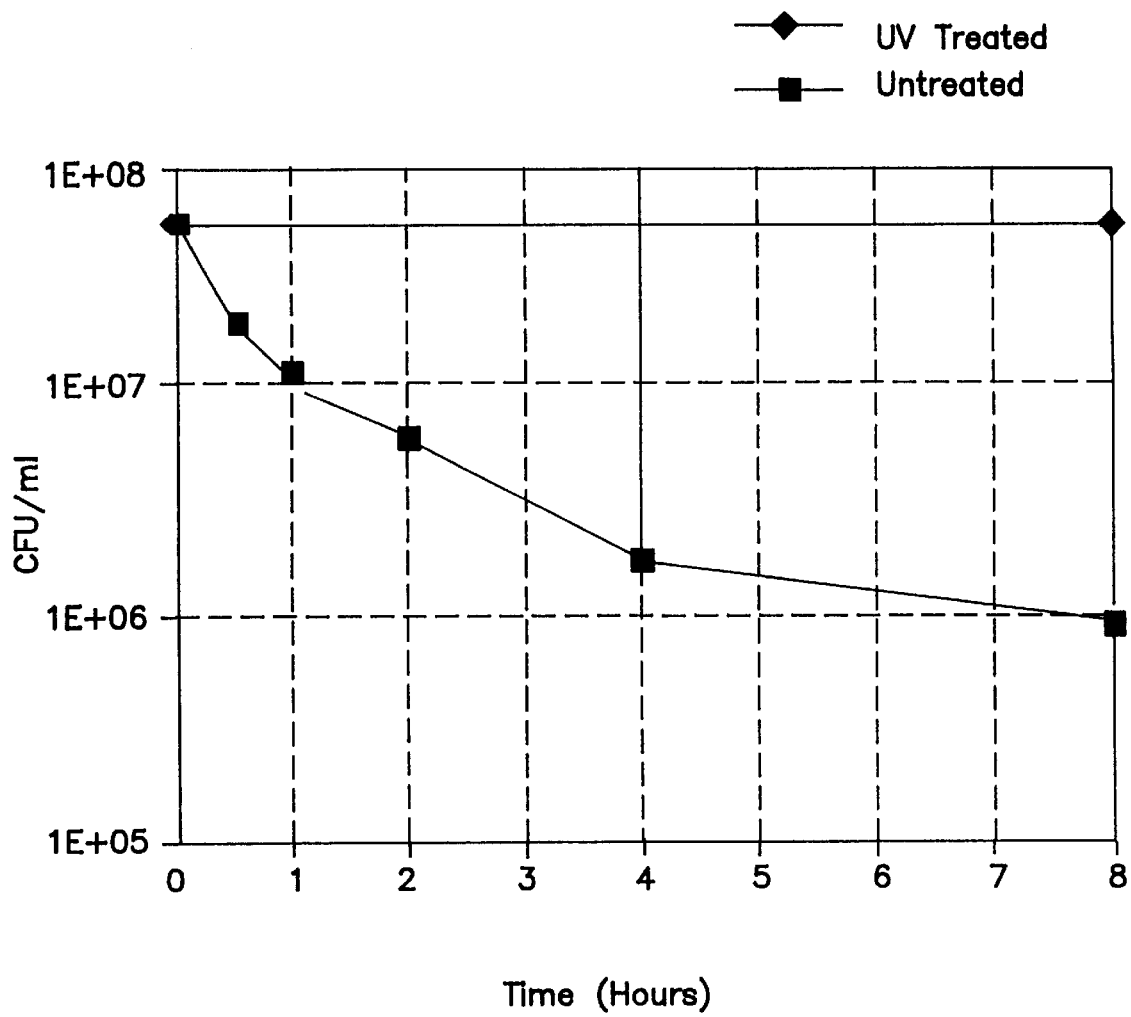
FIG. 7 Bacteriocidal effectiveness during UV treatment at 40 gallons per minute.
Figure 8:
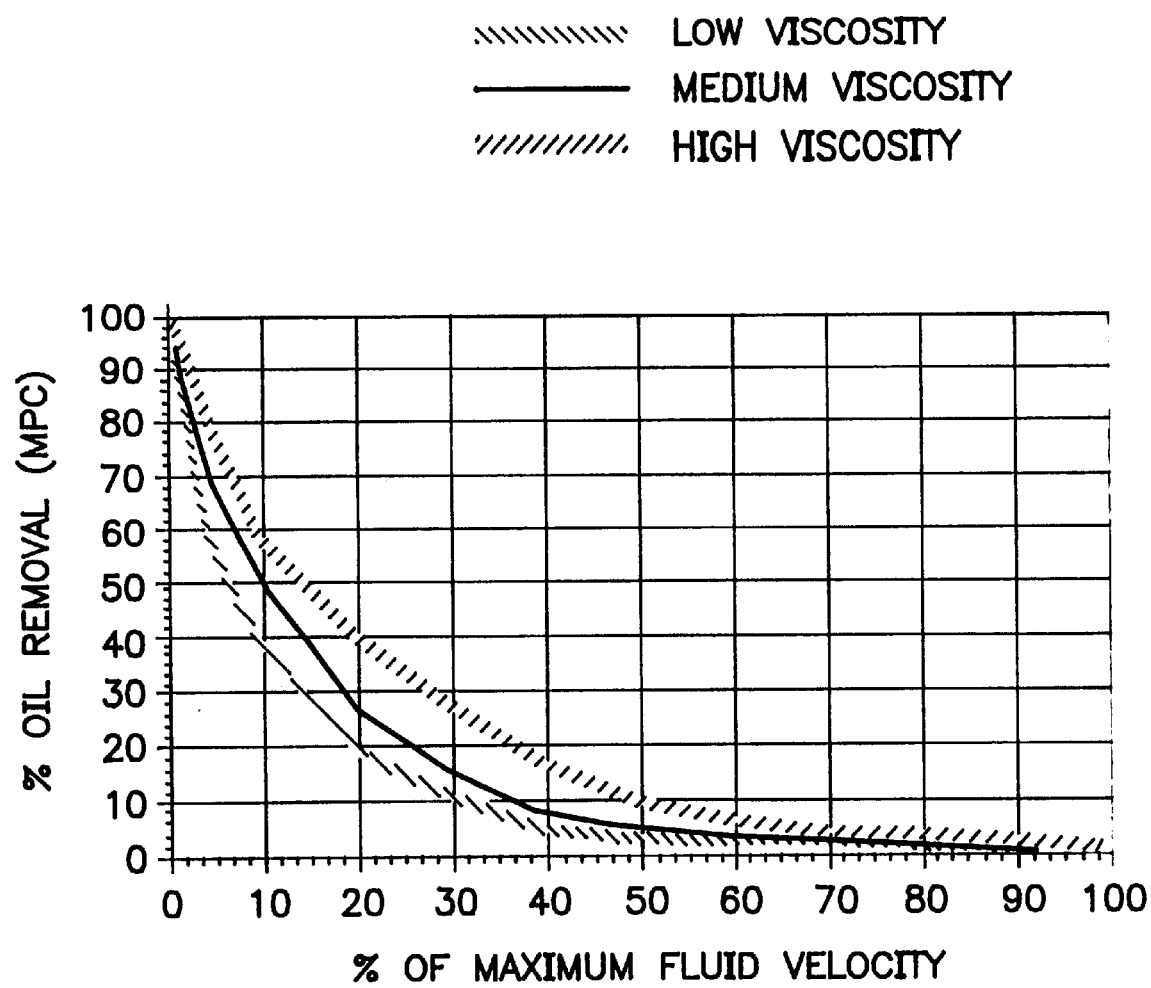
FIG. 8 Expression for percent of oil removal for UV effectiveness as a function of percent maximum fluid velocity in the system and viscosity of the oil.
Figure 9:
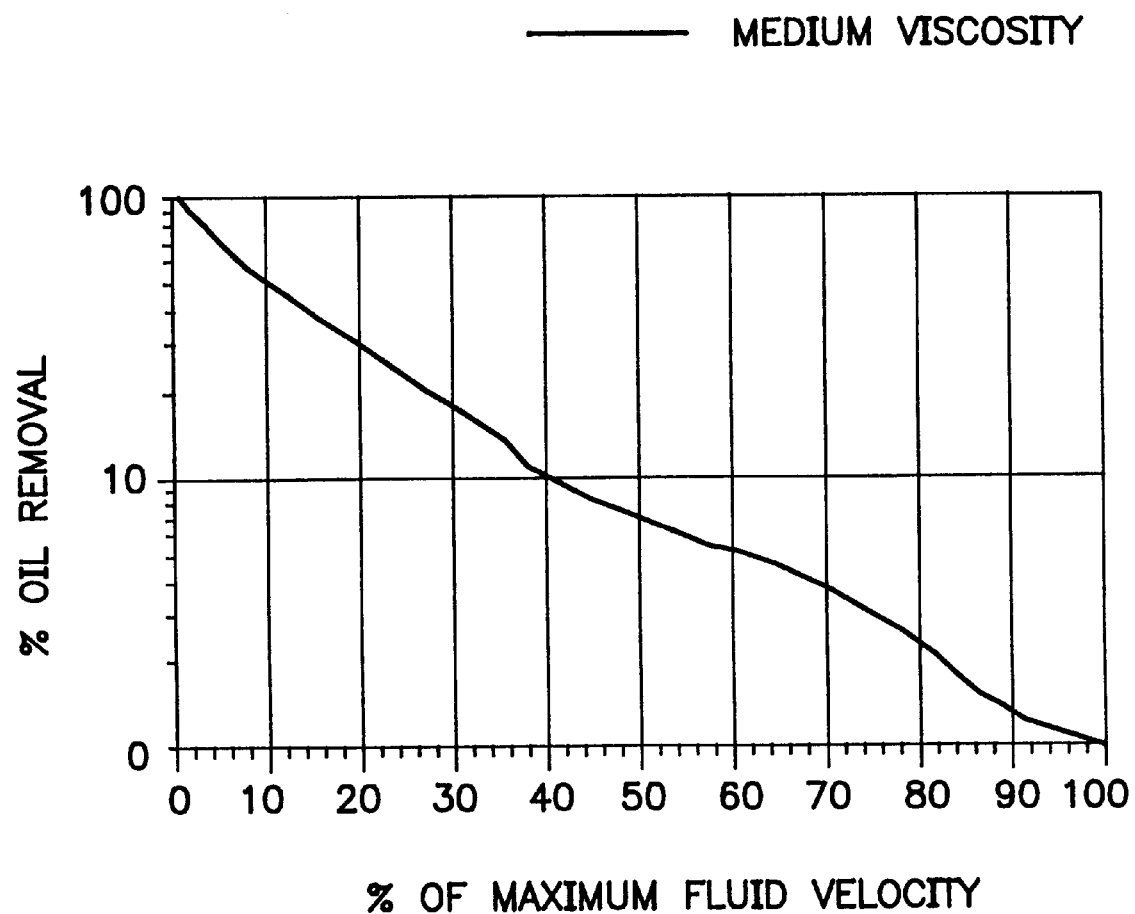
FIG. 9 Expression of degree of oil removal as a function of fluid velocity.

Results from the membrane filtration/plate counting analysis of the coolant are shown in FIG. 7 and Table 5. The number of bacteria cultured from the coolant in the recycling reservoir decreased approximately 50-fold during the course of the 8 hour treatment. As observed in Run I, the most effective killing rate occurred within the first hour of treatment (FIG. 6). The decrease in bactericidal effectiveness observed may be due to the initial removal of highly suspectable organisms within the first few passes through the apparatus, followed by a process of repeated UV exposure needed to kill more resistant bacteria.

TABLE 5

Run II: Analysis of Reservoir CFUs

| Time (Minutes) | Sample Location | Total Gal. Treated | Bacteria (CFU/ml) | Bacteria (Paddle) |
| --- | --- | --- | --- | --- |
| 0 | Reservoir | 0 | 5.76E + 07 | >1E + 07 |
| 30 | Reservoir | 1200 | 2.05E + 07 | >1E + 07 |
| 60 | Reservoir | 2400 | 1.09E + 07 | 1E + 07 |
| 120 | Reservoir | 4800 | 5.98E + 06 | 1E + 06 |
| 240 | Reservoir | 9600 | 1.65E + 06 | 1E + 06 |
| 480 | Reservoir | 19200 | 9.29E + 05 | 1E + 05 |
| 480 | Untreated | 0 | 6.67E + 07 | >1E + 07 |

The number of bacterial colonies cultured on the media paddles decreased with increased treatment in the filtration/UV treatment apparatus. These numbers closely matched those obtained with the assays using membrane filtration and culturing on TSA plates (Table 5). Results from this assay also indicated that more bacteria survived the filtration/UV treatment at a flow rate of 40 gallons per minute for 8 hours than survived in Run I at a flow rate of 10 gallons/minute after 8 hours treatment.

Treatment of highly contaminated industrial coolant demonstrated that the filtration/UV irradiation apparatus was highly effective in killing bacteria present in the fluid. This bacterial killing was observed in two separate runs of the apparatus. The most effective bacterial killing was observed when the unit was run at a flow rate of 10 gallons per minute, in which a 5-log decrease in culturable bacteria was observed after a 24-hour recycling treatment of 25 gallons of highly contaminated coolant ($10^7$ CFU/ml).

Thus, effectiveness of this apparatus in disinfecting opaque coolant fluid has been strongly supported in these studies. In addition, the unit ran quietly, and did not cause any overt changes in the make-up or physical behavior of the coolant fluid (e.g. foaming, discoloration, coating, etc.).

Example 4

Fluid Flow Calculations

Fluid flow velocities that prevent occlusion of ultraviolet radiation transmissible tubing have been determined from empirical testing. Increasing velocity of the fluid as a scouring force prevents occlusion as a function of viscosity of the components within the fluid. Thus, the amount of oil that would need to be removed from an oil-contaminated fluid to avoid occlusion can be represented as a function of percent maximum fluid velocity in the UV system at a given tube diameter (Table 6).

TABLE 6

Expression of Oil Removal at Set Tube Diameters

| Removal in Percent | Maximum Velocity in Percent | Tube Diameter (GPM) ¾" | 1" |
|---|---|---|---|
| 10 | 1 | 0.5 | 0.84 |
| 70 | 5 | 2.5 | 4.2 |
| 50 | 10 | 5 | 8.4 |
| 30 | 20 | 10 | 16.8 |
| 18 | 30 | 15 | 25.2 |
| 10 | 40 | 20 | 33.6 |
| 7 | 50 | 25 | 42 |
| 5. | 60 | 30 | 50.4 |
| 4 | 70 | 35 | 58.8 |
| 2. | 80 | 40 | 67.2 |
| 1. | 90 | 45 | 75.6 |
| 1 | 100 | 50 | 84 |

Percentages from Table 6 were determined from the equation:

$$f(x)=-2.345E+1\times ln(x)+1.022E+2(\text{correlation coefficient } R=9.756E-1).$$

These numbers could be altered depending on the viscosity of the contaminant oil (FIG. 8). High viscosity oils had about a 1% to 15% higher percent oil removal than medium viscosity oils. Lower viscosity oils had about a 1% to 10% lower oil percent oil removal than medium viscosity oils. As can be seen, the curve reflects the percent of maximum fluid velocity obtainable. This same data was plotted on a semi-logarithmic scale according to the equation: f(x)=−2.345E+1×ln(x)+1.022E+2 (correlation coefficient R=9.756E-1), as shown in FIG. 9. These numbers were converted with the flow equation: U.S. GPM={ft. per sec.}×{$ID^2$}×{2.45}, to produce the actual gallons per minute (GPM) flow rate for any given tubing. One inch and three quarter inch tube sizes were used as typical sizes. As the tubing becomes larger, it becomes difficult to collect the correct amount of oil to prevent occlusion and this, plus the surface requirement for disinfection, may limit the practical number of gallons that may be treated effectively.

Other embodiments and uses of the invention will be apparent to those skilled in the art from consideration of the specification and practice of the invention disclosed herein. All U.S patents and other documents referenced herein are specifically incorporated by reference. It is intended that the specification and examples be considered exemplary only, with the true scope and spirit of the invention indicated by the following claims.

We claim:

1. An apparatus for disinfecting a contaminated fluid comprising:

a tubing system for guiding the passage of the contaminated fluid at a flow rate (V) through the apparatus comprised of tubing having a flattened to rounded cross section and a portion having ultraviolet-transmissible walls;

a contaminant separation system for removing a minimum percentage of contaminants (MPC), said contaminants comprising living microorganisms, from the contaminated fluid before irradiation according to the equation: MPC=102−(23.45×lnV), wherein V is measured in gallons per minute whereby, as flow rate is increased, the MPC to be removed is decreased; and an ultraviolet radiation system for irradiating the contaminated fluid comprised of a plurality of ultraviolet lamps in close proximity to said portion.

2. An apparatus for disinfecting a contaminated fluid comprising:

a tubing system for guiding the passage of the contaminated fluid at a flow rate (V) through the apparatus comprised of tubing having a flattened to rounded cross section and a portion having ultraviolet-transmissible walls;

a contaminant separation system for removing at least a minimum percentage of contaminants (MPC) from the contaminated fluid before irradiation according to the equation: MPC=102−(23.45×lnV), wherein V is measured in gallons per minute; and an ultraviolet radiation system for irradiating the contaminated fluid comprised of a plurality of ultraviolet lamps in close proximity to said portion, wherein the portion is composed of a perfluoroalkoxy polymer.

3. The apparatus of claim 1 wherein the ultraviolet radiation system is a dry system wherein said plurality of ultraviolet lamps are not in direct contact with said fluid.

4. The apparatus of claim 1 wherein the ultraviolet radiation system comprises ultraviolet lamps submerged in said fluid.

5. The apparatus of claim 1 wherein the tubing system is comprised of an inlet port and an outlet port attached to opposite ends of a coiled tube.

6. The apparatus of claim 5 wherein the plurality of ultraviolet lamps surround said coiled tube.

7. The apparatus of claim 1 wherein the tubing system comprises a tube within a tube configuration.

8. The apparatus of claim 1 wherein the tubing system generates a thin film of the contaminated fluid during irradiation.

9. The apparatus of claim 8 wherein the thin film has a depth of between about 4 mm to about 2 mm.

10. The apparatus of claim 1 wherein the flow rate is from about 5 to about 10 gallons per minute and the contaminant separator removes at least about 60% to about 50%, respectively, of the contaminants from the contaminated fluid.

11. The apparatus of claim 1 wherein the flow rate is from about 30 to about 60 gallons per minute and the contaminant separator removes at least about 25% to about 6%, respectively, of the contaminants from the contaminated fluid.

12. The apparatus of claim 1 wherein the ultraviolet radiation system further comprises a plurality of ultraviolet reflectors positioned to direct ultraviolet radiation toward said contaminated fluid.

13. The apparatus of claim 12 wherein the reflectors are coated with an ultraviolet reflective material.

14. The apparatus of claim 13 wherein the ultraviolet reflective material is selected from the group consisting of an aluminum, a titanium, a titanium nitrate or a combination thereof.

15. The apparatus of claim 1 further comprising a turbulence-generating system for creating turbulence within said industrial fluid during irradiation.

16. The apparatus of claim 15 wherein the turbulence-generating system comprises intratubular ribbons, paddles, beads, cones, vanes, or combinations thereof.

17. An apparatus for disinfecting a contaminated fluid comprising:
- a tubing system for guiding the passage of the contaminated fluid at a flow rate (V) through the apparatus comprised of tubing having a flattened to rounded cross section and a portion having ultraviolet-transmissible walls;
- a contaminant separation system for removing at least a minimum percentage of contaminants (MPC) from the contaminated fluid before irradiation according to the equation: MPC=102−(23.45×1 nV), wherein V is measured in gallons per minute;
- an ultraviolet radiation system for irradiating the contaminated fluid comprised of a plurality of ultraviolet lamps in close proximity to said portion; and
- a turbulence-generating system for creating turbulence within said contaminated fluid during irradiation, wherein the turbulence-generating system comprises a pressure differential.

18. An apparatus for disinfecting a contaminated fluid comprising:
- a tubing system for guiding the passage of the contaminated fluid at a flow rate (V) through the apparatus comprised of tubing having a flattened to rounded cross section and a portion having ultraviolet-transmissible walls;
- a contaminant separation system for removing at least a minimum percentage of contaminants (MPC) from the contaminated fluid before irradiation according to the equation: MPC=102−(23.45×1 nV), wherein V is measured in gallons per minute;
- an ultraviolet radiation system for irradiating the contaminated fluid comprised of a plurality of ultraviolet lamps in close proximity to said portion; and
- a turbulence-generating system for creating turbulence within said contaminated fluid during irradiation, wherein the turbulence-generating system comprises aeration provided from a tube within a tube mechanism.

19. An apparatus for disinfecting a contaminated fluid comprising:
- a tubing system for guiding the contaminated fluid through the apparatus at a flow rate (V) comprised of ultraviolet-transmissible tubing having a flattened to rounded cross section;
- a turbulence-generating system for creating turbulence within said contaminated fluid during irradiation; and
- an ultraviolet radiation system for irradiating the contaminated fluid comprised of a plurality of ultraviolet lamps in close proximity to said UV transmissible tubing, wherein the turbulence-generating system comprises a pressure differential or aeration within the fluid.

20. An apparatus for disinfecting a contaminated fluid comprising:
- a tubing system for guiding the contaminated fluid through the apparatus at a flow rate (V) comprised of ultraviolet-transmissible tubing having a flattened to rounded cross section;
- a turbulence-generating system for creating turbulence within said contaminated fluid during irradiation;
- an ultraviolet radiation system for irradiating the contaminated fluid comprised of a plurality of ultraviolet lamps in close proximity to said UV transmissible tubing; and
- a contaminant separation system for removing a minimum percentage of contaminants (MPC), said contaminants comprising living microorganisms, from the contaminated fluid before irradiation according to the equation: MPC=102−(23.45×lnV), wherein V is measured in gallons per minute, whereby as flow rate is increased, the MPC to be removed is decreased.

21. An apparatus for disinfecting a contaminated fluid comprising:
- a tubing system for guiding the contaminated fluid through the apparatus at a flow rate (V) comprised of ultraviolet-transmissible tubing having a flattened to rounded cross section;
- a turbulence-generating system for creating turbulence within said contaminated fluid during irradiation;
- an ultraviolet radiation system for irradiating the contaminated fluid comprised of a plurality of ultraviolet lamps in close proximity to said UV transmissible tubing; and
- a contaminant separation system for removing a minimum percentage of contaminants (MPC) from the contaminated fluid before irradiation according to the equation: MPC=102−(23.45×lnV), wherein V is measured in gallons per minute, wherein the MPC is adjusted up to about 10% to account for a viscosity differential between uncontaminated fluid and a contaminant within said contaminated fluid.

* * * * *